US012788098B2

(12) United States Patent
Righi et al.

(10) Patent No.: US 12,788,098 B2
(45) Date of Patent: Nov. 10, 2026

(54) PROTECTIVE HELMET EQUIPPED WITH VISOR WITH FRAME AND LC LAYER

(71) Applicant: OUT OF S.R.L., Brescia (IT)

(72) Inventors: Federico Righi, Brescia (IT); Roberto Righi, Brescia (IT)

(73) Assignee: OUT OF S.R.L., Brescia (IT)

( * ) Notice: Subject to any disclaimer, the term of this patent is extended or adjusted under 35 U.S.C. 154(b) by 365 days.

(21) Appl. No.: 18/290,169

(22) PCT Filed: Jun. 1, 2022

(86) PCT No.: PCT/IB2022/055115
§ 371 (c)(1),
(2) Date: Nov. 10, 2023

(87) PCT Pub. No.: WO2022/254352
PCT Pub. Date: Dec. 8, 2022

(65) Prior Publication Data

US 2024/0277099 A1 Aug. 22, 2024

(30) Foreign Application Priority Data

Jun. 4, 2021 (IT) ........................ 102021000014558

(51) Int. Cl.
*A42B 3/00* (2006.01)
*A42B 3/06* (2006.01)
(Continued)

(52) U.S. Cl.
CPC ................ *A42B 3/224* (2013.01); *A42B 3/06* (2013.01); *A61F 9/023* (2013.01); *A61F 9/029* (2013.01);
(Continued)

(58) Field of Classification Search
CPC ....... A42B 3/224; A42B 3/06; G02F 1/13312; G02F 1/13324; A61F 9/023; A61F 9/029
See application file for complete search history.

(56) References Cited

U.S. PATENT DOCUMENTS 4,749,261 A 6/1988 Mclaughlin et al.
5,315,099 A * 5/1994 Gunz ...................... A61F 9/067 349/122

(Continued)

FOREIGN PATENT DOCUMENTS

DE 102005001804 A1 * 7/2006 ............. A42B 3/224
DE 102005044722 A1 * 3/2007 ............... A42B 3/24

(Continued)

OTHER PUBLICATIONS

International Search Report for International Patent Application No. PCT/IB2022/055115, mailed Sep. 16, 2022.

(Continued)

*Primary Examiner* — Richale L Quinn
(74) *Attorney, Agent, or Firm* — CANTOR COLBURN LLP

(57) ABSTRACT

A protective helmet for practicing sports activities or using motorized vehicles is provided. The protective helmet has a cap provided with a front opening at an eye region of a user, and closed by a visor assembly. The visor assembly has at least one at least partially transparent structural lens, a guest-host type liquid crystal (LC) film adapted to modify its own transparency level, arranged behind the at least partially transparent structural lens, at least one electrical source for powering the LC film, and a frame for supporting the at least partially transparent structural lens and anchoring the at least partially transparent structural lens to the cap. The frame follows at least partially a perimeter of the at least partially transparent structural lens.

10 Claims, 4 Drawing Sheets

(51) Int. Cl.

| | |
|---|---|
| ***A42B 3/22*** | (2006.01) |
| ***A61F 9/02*** | (2006.01) |
| ***G02F 1/133*** | (2006.01) |
| ***G02F 1/137*** | (2006.01) |

(52) U.S. Cl.

CPC ...... *G02F 1/13312* (2021.01); *G02F 1/13324* (2021.01); *G02F 1/13725* (2013.01)

(56) References Cited

U.S. PATENT DOCUMENTS

| | | | | | |
|---|---|---|---|---|---|
| 5,671,483 | A * | 9/1997 | Reuber | A42B 3/245 2/435 |
| 6,047,409 | A | 4/2000 | Simpson | |
| 7,567,306 | B2 * | 7/2009 | Park | A61F 9/023 349/13 |
| 9,295,297 | B2 * | 3/2016 | Wilson | B32B 7/023 |
| 9,801,425 | B2 * | 10/2017 | Ahn | A42B 3/24 |
| 9,918,508 | B2 * | 3/2018 | Ryan | A42B 3/226 |
| 10,357,076 | B2 * | 7/2019 | Lipkens | A42B 3/222 |
| 11,096,440 | B2 * | 8/2021 | Tsai | A42B 3/24 |
| 11,458,338 | B2 * | 10/2022 | Wilson | A62B 18/003 |
| 12,048,652 | B2 * | 7/2024 | Righi | A61F 9/029 |
| 12,342,897 | B2 * | 7/2025 | Righi | A42B 3/226 |
| 2002/0159159 | A1 * | 10/2002 | Wilson | B32B 27/36 359/630 |
| 2005/0007548 | A1 * | 1/2005 | Ishak | G02C 7/10 351/159.62 |
| 2006/0010572 | A1 * | 1/2006 | Douglas | A42B 3/24 2/231 |
| 2006/0092340 | A1 * | 5/2006 | Blum | G02C 7/08 349/13 |
| 2008/0013000 | A1 * | 1/2008 | Park | A61F 9/023 349/13 |
| 2010/0253603 | A1 * | 10/2010 | Righi | A61F 9/025 345/8 |
| 2011/0283431 | A1 * | 11/2011 | Miller, IV | G02C 7/101 2/10 |
| 2014/0223641 | A1 * | 8/2014 | Henderson | A42B 3/065 2/411 |
| 2015/0272260 | A1 | 10/2015 | Ryan et al. | |
| 2020/0126499 | A1 * | 4/2020 | Huang | G09G 3/3607 |
| 2021/0058695 | A1 * | 2/2021 | Unger | H04R 5/033 |
| 2022/0269122 | A1 * | 8/2022 | Huang | A42B 3/042 |
| 2025/0331596 | A1 * | 10/2025 | Levesque | A42B 3/245 |

FOREIGN PATENT DOCUMENTS

| | | | | | |
|---|---|---|---|---|---|
| EP | 0238164 | A1 | | 9/1987 | |
| EP | 1764007 | A2 | * | 3/2007 | A42B 3/24 |
| EP | 2768333 | A1 | | 8/2014 | |
| JP | H08232111 | A | | 9/1996 | |
| KR | 20040086985 | A | | 10/2004 | |
| WO | 2010088596 | A1 | | 8/2010 | |
| WO | WO-2013057745 | A1 | * | 4/2013 | A42B 3/225 |
| WO | WO-2014078380 | A1 | * | 5/2014 | B32B 37/18 |
| WO | WO-2016207743 | A1 | * | 12/2016 | A42B 3/226 |
| WO | WO-2021174321 | A1 | * | 9/2021 | A42B 3/224 |

OTHER PUBLICATIONS

Written Opinion for International Patent Application No. PCT/IB2022/055115, mailed Sep. 16, 2022.

Japanese Office Action for corresponding application 2023-574440; Mail date Mar. 10, 2026.

* cited by examiner

PROTECTIVE HELMET EQUIPPED WITH VISOR WITH FRAME AND LC LAYER

CROSS-REFERENCE TO RELATED APPLICATIONS

This application is a National Phase Application of PCT International Application PCT/IB2022/055115, having an International Filing Date of Jun. 1, 2022 which claims priority to Italian Application No. 102021000014558 filed Jun. 4, 2021, each of which is hereby incorporated by reference in its entirety.

FIELD OF THE INVENTION

The subject of the present invention is a protective helmet equipped with an eye visor for the practice of sports activities and/or the use of motorized vehicles.

BACKGROUND OF THE INVENTION

Protective helmets often include a protective eye visor. In some cases this visor is only intended to protect the user's eyes against the entry of debris, dust, or simply against the wind. In other cases, however, the visor also provides protection against excessive light.

Generally, protection from light is achieved simply through the use of pigments that cause the visor to transmit only a fraction of the incident light. Filters of this type are generally classified into categories (S0, S1, S2, etc.) with increasing levels of absorption. However, in many situations, the user needs to have a level of light filtering that varies according to the different levels of external brightness, such as in the case of a motorcyclist going from a sunny area through a tunnel.

Technologies that seek a solution to this problem are known. However, such known technologies have limitations that actually make them ineffective.

Photochromatic lenses are known to be made with treatments or materials that react to sunlight causing the lens to darken. Such known lenses, however, are all too slow to react to very rapid changes in brightness. Furthermore, the optimal substrate on which to carry out such treatments is glass, which is a material that is hardly compatible with protective devices.

Electrochromic lenses are known that typically use polymers that may change optical properties when a magnetic field is applied. Said lenses, while faster than photochromatic lenses, are still quite slow. Moreover, the high power required to achieve the change of state limits the maximum number of possible changes, making this type of lens functional for automatic adaptation to ambient light only in the presence of bulky batteries.

Finally, lenses that use layers of liquid crystals are known, and they are the only ones that are able to react quickly to changes in ambient light. However, lenses of this type are still substantially unused, given the persistence of a number of issues, including: low maximum brightness of the filter, presence of unwanted polarizations, interference with other transparent elements, and undesirable reactions to mechanical stresses. For these reasons, said lenses find application in the field of protective devices for welding, wherein TN (twisted nematic)-type planar liquid crystal LC screens are widely used. However, said screens are not suitable for sunlight protection under normal conditions, being in fact too dark in their maximum transmission state and having a very small field of vision.

Device application techniques using GH (Guest-Host)-type liquid crystals are also known. This type of liquid crystal does not use polarizing filters and may therefore achieve transparencies much greater than 50 percent, making it potentially more suitable for use in sunlight protective devices under normal conditions. However, there are a number of issues with this type of lens as well. In fact, GH-type liquid crystal LC filters react to mechanical stresses by creating unwanted inhomogeneities in the level of transparency. Most existing helmet visors are made in such a way that, when a GH-type LC layer is applied to them, said layer undergoes such deformations and mechanical stresses that the uniformity of its transparency is compromised. Furthermore, helmet visors are typically made using the injection molding technique, which generates parts with residual internal stresses that interfere with the liquid crystals, creating a birefringence effect typically called "rainbow" that makes the vision uncomfortable.

SUMMARY OF THE INVENTION

The object of the present invention is to solve the problems found in the state of the art in order to obtain a helmet equipped with a variable transparency visor that is truly effective and comfortable to use.

Said object is achieved by a protective helmet as described and claimed herein. Advantageous embodiments of the present invention are also described.

BRIEF DESCRIPTION OF THE FIGURES

The features and advantages of the protective helmet according to this invention will become apparent from the following description, given as a non-limiting example in accordance with the accompanying drawings, wherein.

DETAILED DESCRIPTION

Figure 1:
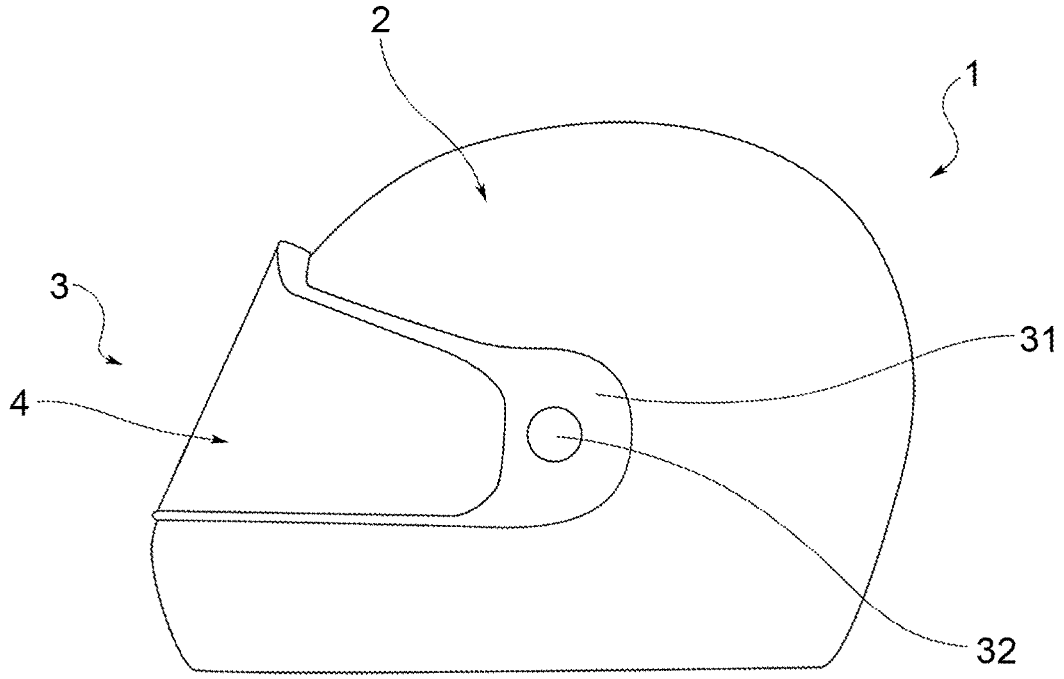
FIG. 1 is a side view of a protective helmet according to the present invention in one embodiment.
Figure 2:
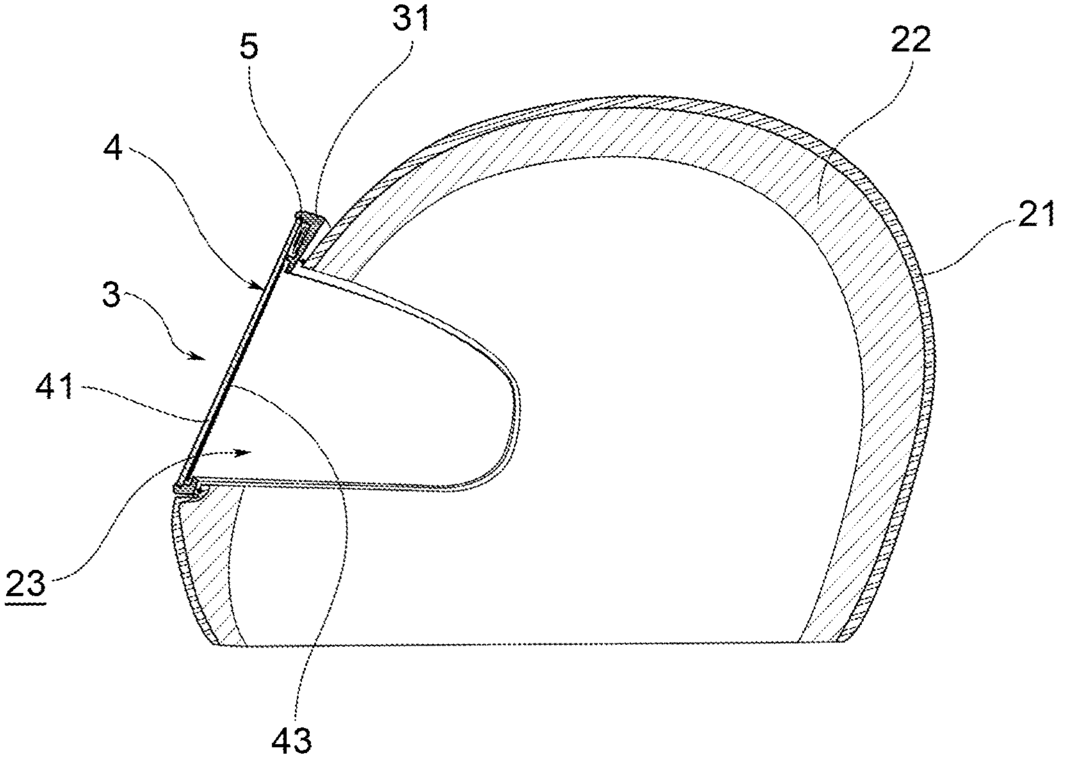
FIG. 2 is a cross-sectional view of the protective helmet of FIG. 1.
Figure 3:
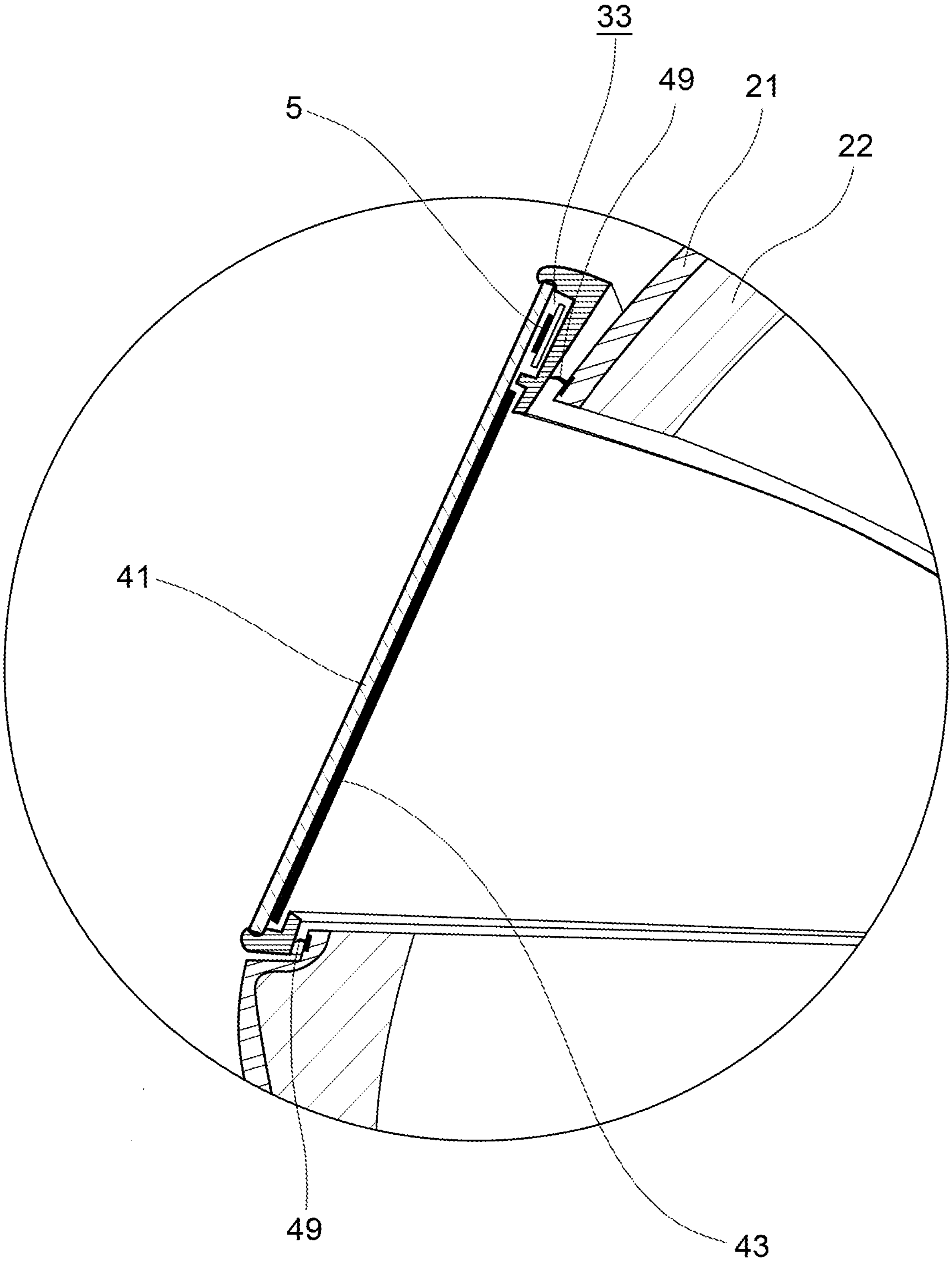
FIG. 3 shows a detail of the visor of the helmet of FIG. 1.

With reference to the appended figures, 1 has been used to collectively denote a protective helmet equipped with a visor for the eyes for the practice of sports activities or the use of motorized vehicles according to the present invention.

The helmet 1 comprises a cap 2, protecting at least part of the user's head, to which is engaged a visor assembly 3, protecting the user's eyes.

The cap 2 comprises a rigid outer shell 21, such as made of plastics or composite, and a collapsible inner shell 22, such as made of polyurethane foam or expanded 10 polystyrene.

The inner shell 22 is covered, on the side intended to be in contact with the user's head, with padding, made mainly of fabric, adapted to improve comfort during the use of the helmet.

Preferably, the cap 2 is equipped with a communication system. For example, the helmet 1 comprises a bone conduction audio system.

Preferably, the cap 2 may also include additional components typical of a helmet, such as vents, spoilers, aerodynamic appendages, signal lights, communication systems, and displays.

The cap 2 has a frontal opening 23 at the user's eye region, which is intended to be closed by the visor assembly 3 at least when the helmet 1 is being used. Said opening is characterized by a closed perimeter in the case of full-face helmets (as in FIG. 1), while it takes the form of a recess in the perimeter of the cap in the case of helmets without chin guards (as in FIG. 4).

The cap 2 has, on both sides, a seat arranged near the region of the user's ear, adapted to accommodate a corresponding anchor pin 32 of the visor assembly 3 so that said assembly is pivoted on the cap 2 to open and/or close the opening 23.

In one embodiment, the visor assembly 3 is attached to the cap 2.

In a further embodiment, the visor assembly 3 is removable from the cap 2, for example, to be replaced with a different visor assembly to adapt the helmet 1 to specific lighting situations.

The visor assembly 3 comprises a variable transparency lens assembly 4 that is truly effective and comfortable in use.

The visor assembly 3 comprises a frame 31 engageable to the cap 2 and adapted to support the lens assembly 4. Therefore, in this embodiment, a frame 31 is applied to the lens assembly 4, and in particular to a structural lens 41, which at least partially follows the perimeter of said structural lens 41.

Preferably, the frame is configured to make a seal with the sealing gaskets 49 of the opening 23 and to prevent the passage of light outside the outer perimeter of the LC film 43.

Figure 4:
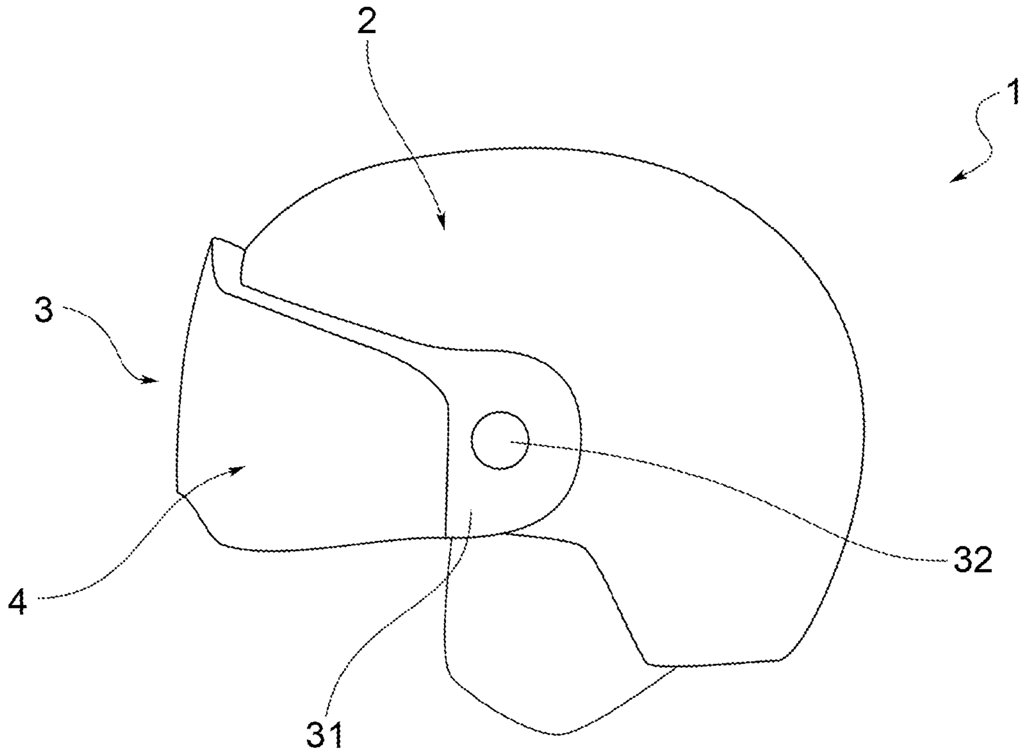
FIG. 4 is a side view of a protective helmet according to the present invention, in a further embodiment.
Figure 5:
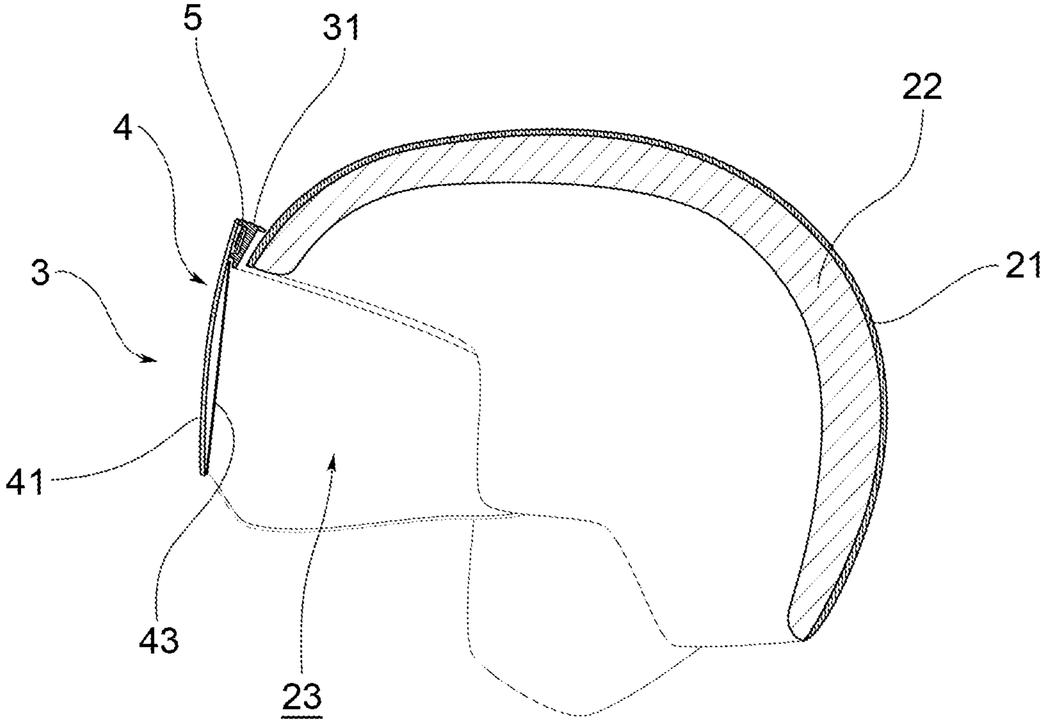
FIG. 5 is a cross-sectional view of the protective helmet of FIG. 4.

In the embodiment in FIGS. 1 and 4, the visor assembly 3 comprises a frame 31 that is engageable to the cap 2 by means of a pair of anchor pins 32 that are insertable into the appropriate seats of the cap 2.

In the embodiment of FIG. 1, the frame 31 completely surrounds the lens assembly 4 of the visor 3. In said embodiment, the cap 2 also comprises a chin guard, fixed or flip-up, to cover the user's chin. In said embodiment, the helmet 1 is a full-face helmet.

In the embodiment in FIG. 4, the frame 31 only partially surrounds the lens assembly 4 of the visor 3.

In fact, as may be seen, the lower part of the lens assembly 4 is without a frame 31. In said embodiment, the cap 2 has no chin guard covering the user's chin, which therefore remains uncovered. In said embodiment, the helmet 1 is an open or non-full-face helmet.

Figure 6:
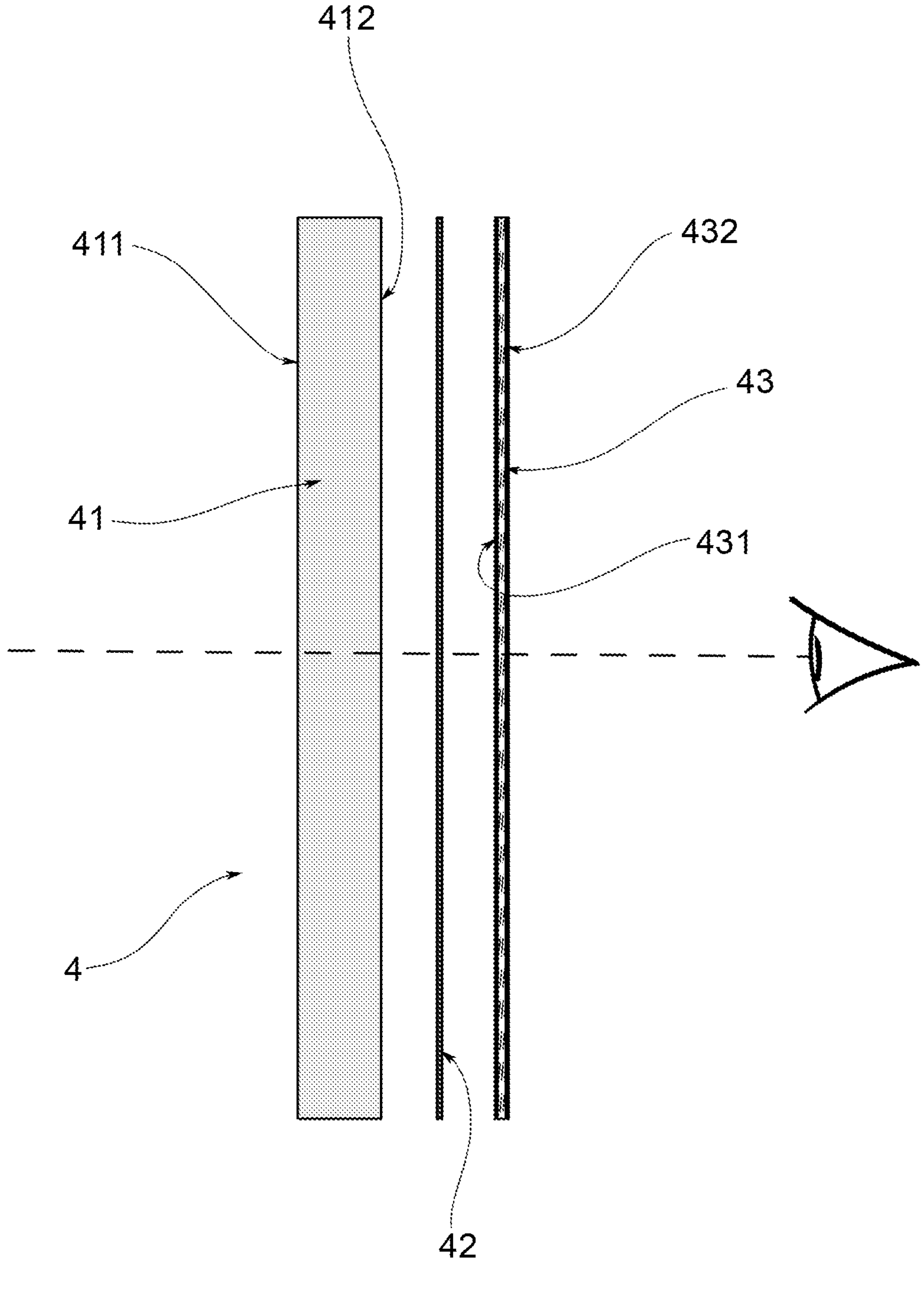
FIG. 6 is an exploded diagram of the structure of the lens assembly of the visor of the protective helmet, in one embodiment.

As shown for example in FIG. 6, the lens assembly 4 comprises a structural lens 41 or outer lens. The structural lens 41 is at least partially transparent.

Said lens may be made with transparent materials and without the addition of pigments resulting in a light transmission close to 100 percent. Or it may be made by using materials or combinations of pigments, materials, and surface treatments in such a way as to filter out some of the non-visible light or radiation, even possibly unevenly over the whole spectrum to achieve optimal vision under different environmental conditions.

The structural lens 41 is attached to the frame 31, for example, by interlocking, gluing, by the use of magnets, or by the interposition of double-sided adhesive film.

Preferably the structural lens 41 is made of plastics material, such as polycarbonate or polyamide.

In one embodiment, the structural lens 41 is a thermoformed sheet, obtained by thermoforming or flexing a sheet of polymeric material. In said embodiment, the visor 3 may possibly be without a depolarizing filter.

In an embodiment intended for use in specific lighting conditions, the structural lens 41 is pigmented to modulate the absorption spectrum, specifically in this case the structural lens 41 may also be pigmented to modulate the contrast in specific lighting situations, for example by increasing it.

The structural lens 41 has an outer surface 411 and an inner surface 412.

Preferably, the outer surface 411 of the structural lens 41 is treated with a coating, such as an anti-scratch, and/or mirroring, and/or anti-reflective, and/or multilayer coating.

The lens assembly 4 comprises a liquid crystal film 43 (hereinafter LC film), provided with an outer face 431, facing the structural lens 41, and an opposite inner face 432.

The LC film 43 is of the GH (Guest-Host) liquid crystal type. In this type of LC film, dichroic pigments are dispersed in a matrix of liquid crystals; the magnetic field drives the orientation of the liquid crystals, which, in turn, drive the orientation of the pigments. Typically in the "active" state, the crystals assume a helical configuration, and the pigments are arranged in planes parallel to the film surface, while in the "inactive" state, crystals and pigments are arranged perpendicular to the surface of the film.

Preferably, the LC film 43 has a visible light transparency of at least 60 percent in the lightest state thereof and at most 40 percent in the darkest state thereof. For example, the LC layer may have a transparency of about 30 percent in the darkest state thereof and about 70 percent in the lightest state thereof.

The LC film 43 is controlled by an electronic board 5, described below, which produces a signal, the intensity of which increases with the increase in ambient light.

Preferably, the LC film 43 is mounted in back of the structural lens 41, i.e., on the side of the inner surface 412, preferably using optically clear adhesive (OCA).

In one embodiment, shown for example in FIG. 1, the structural lens 41 has a cylindrical curvature, that is, it is curved on a single axis. Advantageously, this shape allows the LC film 43 to be laminated to the structural lens 41 in an optimal manner.

Preferably, internally to the LC film 43, i.e., on the side of the inner face 432, anti-fog and/or anti-reflection treatments, or a real additional layer equipped with anti-fog and/or anti-reflection treatment, may be applied.

In an embodiment shown in FIG. 6, the lens assembly 4 comprises a depolarizing film 42 arranged externally to the LC film 43, that is, at the outer face 431. The depolarizing film is 42 then arranged between the structural lens 41 and the LC film 43.

The depolarizing effect is preferably achieved by birefringent film characterized by a wave phase shift between the two optical axes greater than 1500 nm.

The visor assembly 3 comprises an electronic board 5 adapted to control the LC film 43. The electronic board 5 comprises a photovoltaic cell and an electronic circuit powered by the photovoltaic cell. In one embodiment, the electronic board 5 comprises a single photovoltaic cell, arranged in front and center, and two integrated circuits positioned at the rear, sides, and on either side of the photovoltaic cell. Preferably the photovoltaic cell operates simultaneously as a sensor of the amount of light in the environment and as a power supply for the LC film; in fact, the greater the amount of light that strikes the photovoltaic cell, the higher the power generated by the photovoltaic cell; the power with which the LC film is fed is consequently higher and said LC lens darkens more.

Preferably, the response curve between the input signal and output signal from the electronic board 5 may be changed according to the user's needs.

Advantageously, the photovoltaic cell is located close to the structural lens 41, thus receiving more light. Specifically, the electronic board 5 with the photovoltaic cell is located to the rear of the structural lens 41, and the photovoltaic cell faces the structural lens 41.

Preferably, the structural lens 41 has a multilayer mirroring treatment.

Preferably, the electronic board 5 is supported by the frame 31, for example inserted into a frame compartment 33 arranged in an upper portion of said frame and positioned internally with respect to the structural lens 41.

Advantageously, the photovoltaic cell receives filtered light from the structural lens 41 and thus reacts to the same component of ambient light that the user's eye receives, net of the intervention of the LC film.

Preferably, the frame compartment 33 is arranged outside the perimeter defined by the frontal opening 23 of the cap 2, so that, when the visor 3 is lowered, the electronic board 5 is outside the perimeter of the opening 23 and does not result in a significant reduction of the user's field of vision. Advantageously, therefore, the photovoltaic cell is positioned so that it is in an area of the user's field of vision that is already occluded by the cap 2 of the helmet 1.

In one embodiment, the frame compartment 33 is sealed i.e., leak-proof, and protects the electronic board 5; said board may alternatively or additionally be protected by protective coatings or embedded in resins.

In one embodiment, the helmet 1 includes a battery that may provide more power to the electronic board 5; possibly, this battery may also be used to power other electronic devices such as traditional or bone-conduction audio systems, intercoms, "head-up" or traditional displays, signal lights, emergency call systems, cameras, or sensors.

Preferably, the cap 2 comprises a photovoltaic sheet positioned at least partially on the outside of the outer shell 21. Preferably, the photovoltaic sheet is a flexible sheet deformed to follow the curvature of the cap 2. Preferably, the photovoltaic sheet is connected to the battery.

In summary, therefore, the protective helmet 1 for sports or motorized vehicle use according to the present invention comprises:

- a protective cap 2, which, when the helmet is worn, protects at least part of the user's skull;
- a structural lens 41, which is at least partially transparent;
- a GH-type LC film 43 positioned internally to the structural lens 41;
- a frame 31 that follows at least partially the perimeter of the structural lens.

Advantageously, the frame 31 allows for improved stability of the lens to mechanical stresses, protects the LC film 43 from contact with the sealing gaskets 49, and prevents light infiltrations outside the perimeter of the LC film.

Moreover, the frame 31 may possibly be configured as an adaptive interface to adopt cylindrically shaped structural lenses on helmets equipped with openings having a profile that does not lie on a cylindrical surface, but rather for example a spherical or toric surface.

Advantageously, the protective helmet 1 for sports or motorized vehicle use according to the present invention is equipped with a visor with variable transparency that is truly effective and comfortable in use.

It is understood that a person skilled in the art, in order to meet contingent needs, could make modifications to the device described above, all of which are contained within the scope of protection as defined by the following claims.

The invention claimed is:

1. A protective helmet for practicing sports activities or using motorized vehicles, the protective helmet comprising:

a cap provided with a front opening at an eye region of a user, and closed by a visor assembly, wherein the visor assembly comprises:

at least one at least partially transparent structural lens;

a guest-host type liquid crystal (LC) film adapted to modify its own transparency level, arranged behind the at least partially transparent structural lens;

at least one electrical source for powering the LC film; and a frame adapted to support the at least partially transparent structural lens and anchor the at least partially transparent structural lens to the cap, and wherein said frame at least partially follows a perimeter of said at least partially transparent structural lens, and wherein said frame is configured to make a seal with sealing gaskets of the front opening and to prevent the passage of light outside an outer perimeter of the LC film.

2. The protective helmet of claim 1, wherein said LC film has a transparency to visible light of at least 60% in the lightest state thereof and at most 40% in the darkest state thereof.

3. The protective helmet of claim 1, wherein said electrical source for powering the LC film is connected to an electronic board that controls the LC film and produces a signal, and wherein an intensity of the signal increases with increasing ambient light.

4. The protective helmet of claim 3, wherein the electronic board is provided with a response curve, between an input signal and an output signal, which is modifiable according to needs of the user.

5. The protective helmet of claim 3, wherein said electronic board is accommodated in a frame compartment arranged outside a perimeter defined by the front opening of the cap so as not to obstruct a field of vision of the user.

6. The protective helmet of claim 1, wherein said at least partially transparent structural lens is provided with a multilayer mirroring treatment.

7. The protective helmet of claim 1, wherein the visor assembly further comprises at least one depolarizing layer arranged between the at least partially transparent structural lens and the LC film.

8. The protective helmet of claim 1, wherein the at least partially transparent structural lens is a thermoformed sheet of polymer material.

9. The protective helmet of claim 1, wherein said cap comprises:

a rigid outer shell and a collapsible inner shell; and a photovoltaic plate positioned at least partially outside the rigid outer shell, said photovoltaic plate being connected directly to the electrical source for powering the LC film, or by interposition of a battery.

10. The protective helmet of claim 1, wherein said cap comprises:

a rigid outer shell and a collapsible inner shell, and a bone conduction audio system.

* * * * *